United States Patent
Sato

(10) Patent No.: US 7,876,275 B2
(45) Date of Patent: Jan. 25, 2011

(54) ELECTRONIC DEVICE

(75) Inventor: Tsutomu Sato, Ome (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/608,615

(22) Filed: Oct. 29, 2009

(65) Prior Publication Data

US 2010/0164813 A1 Jul. 1, 2010

(30) Foreign Application Priority Data

Dec. 25, 2008 (JP) ............................. 2008-331342

(51) Int. Cl.
*H01Q 1/24* (2006.01)
(52) U.S. Cl. ...................................... 343/702
(58) Field of Classification Search .......... 343/700 MS, 343/702, 741, 866
See application file for complete search history.

(56) References Cited

U.S. PATENT DOCUMENTS

| | | | |
|---|---|---|---|
| 5,646,635 A * | 7/1997 | Cockson et al. ............. | 343/702 |
| 5,943,018 A * | 8/1999 | Miller ......................... | 343/702 |
| 5,949,379 A * | 9/1999 | Yang .......................... | 343/702 |
| 6,758,689 B1 * | 7/2004 | Bair et al. ................... | 439/136 |
| 7,042,405 B2 * | 5/2006 | Peng .......................... | 343/702 |

FOREIGN PATENT DOCUMENTS

| | | |
|---|---|---|
| JP | 56-69107 U | 6/1981 |
| JP | H09-148824 A | 6/1997 |
| JP | 2003-209482 | 7/2003 |
| JP | 2004-056773 | 2/2004 |
| JP | 3517879 | 2/2004 |

OTHER PUBLICATIONS

The Notice of Reasons for Rejection for Japanese Patent Application No. 2008-331342 mailed by the Japan Patent Office on Dec. 15, 2009 along with an English translation thereof and Statement of Accuracy of Translation in five (5) pages.
Explanation of Non-English Language References.

\* cited by examiner

*Primary Examiner*—Tan Ho
(74) *Attorney, Agent, or Firm*—Knobbe, Martens, Olson & Bear LLP

(57) ABSTRACT

According to one embodiment, an electronic device includes a housing, an antenna and a supporting portion. The antenna has a communication face. The supporting portion is between the housing and the antenna. The supporting portion is configured to support the antenna to be slidable between the first position where the antenna is inside the housing and the second position where the antenna is out of the housing, and also to be pivotable at the second position.

9 Claims, 6 Drawing Sheets

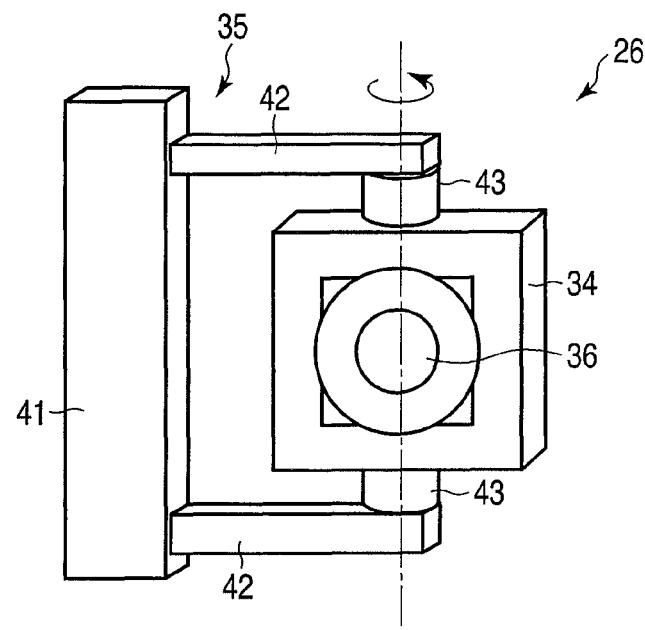
F I G. 2
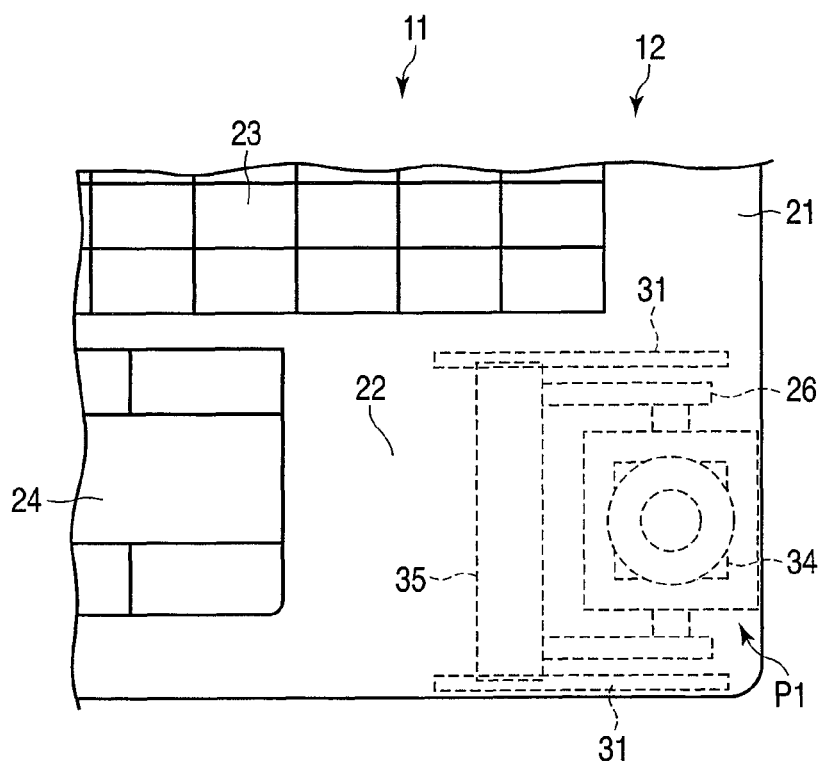
F I G. 3

ELECTRONIC DEVICE

CROSS-REFERENCE TO RELATED APPLICATIONS

This application is based upon and claims the benefit of priority from Japanese Patent Application No. 2008-331342, filed Dec. 25, 2008, the entire contents of which are incorporated herein by reference.

BACKGROUND

1. Field

One embodiment of the present invention relates to an electronic device equipped with an antenna used for radio communications.

2. Description of the Related Art

Jpn. Pat. Appln. KOKAI Publication No. 2003-209482 discloses a folding mobile terminal with a built-in GPS antenna. The mobile terminal includes an operation portion, a display portion open/closed with respect to the operation portion, a GPS antenna housed inside the display portion and a pivot mechanism which pivots the portion where the GPS antenna is mounted. The pivot mechanism is installed within the display portion, and it includes a slide member which slides as interlocked with the opening/closing of the display portion and a conversion member which converts the sliding motion of the slide member into a rotating motion.

In this mobile terminal, the slide member and conversion member actuate as the display portion is opened or closed and thus the direction of the GPS antenna is pivoted by 180 degrees. In this manner, the direction of the GPS antenna is optimized at all times.

It should be noted here that in short-distance radio communications of recent years, there is, for example, Transfer Jet (registered trademark) as a standard for radio communications of the type in which the limitation of communication distance is very strict. In the radio communications of this communication standard, the distance in which communications can be established between instruments is only several centimeters. For this reason, if the antenna is not set in an appropriate direction, radio communications cannot be established well in some cases. Further, there are increasing trends in which the style of radio communications between electronic devices diversifies, and therefore merely pivoting the antenna as interlocked with the opening/closing of the display portion as discussed above cannot follow such various styles of radio communication modes sufficiently. Furthermore, in electronic devices of recent years, there is a trend of thinning the devices by controlling the thickness. Here, if a pivot mechanism is installed simply inside the display portion, the thickness of the device is increased. Under these circumstances, the above-described structure cannot be directly employed.

BRIEF DESCRIPTION OF THE SEVERAL VIEWS OF THE DRAWINGS

A general architecture that implements the various feature of the invention will now be described with reference to the drawings. The drawings and the associated descriptions are provided to illustrate embodiments of the invention and not to limit the scope of the invention.

FIG. 2 is an exemplary diagram showing a perspective view of an antenna unit contained in the housing of the portable computer shown in FIG. 1;

FIG. 3 is an exemplary top view of the antenna unit shown in FIG. 1 while it is in the first portion;

DETAILED DESCRIPTION

Various embodiments according to the invention will be described hereinafter with reference to the accompanying drawings. In general, according to one embodiment of the invention, an electronic device includes a housing, an antenna and a supporting portion. The antenna has a communication face. The supporting portion is between the housing and the antenna. The supporting portion is configured to support the antenna to be slidable between the first position where the antenna is inside the housing and the second position where the antenna is out of the housing, and also to be pivotable at the second position.

Embodiments of the electronic device will now be described with reference to FIGS. 1 to 8. In this embodiment, a case where the present invention is applied to a portable computer, which is the so-called notebook personal computer, as an example of the electronic device will be discussed. In this specification, the near side to the user (that is, user side) is defined as front, the far side from the user is rear, the left-hand side of the user is left, the right-hand side of the user is right, the upper side from the user's position is up and the lower side from the user's position is down.

Figure 1:
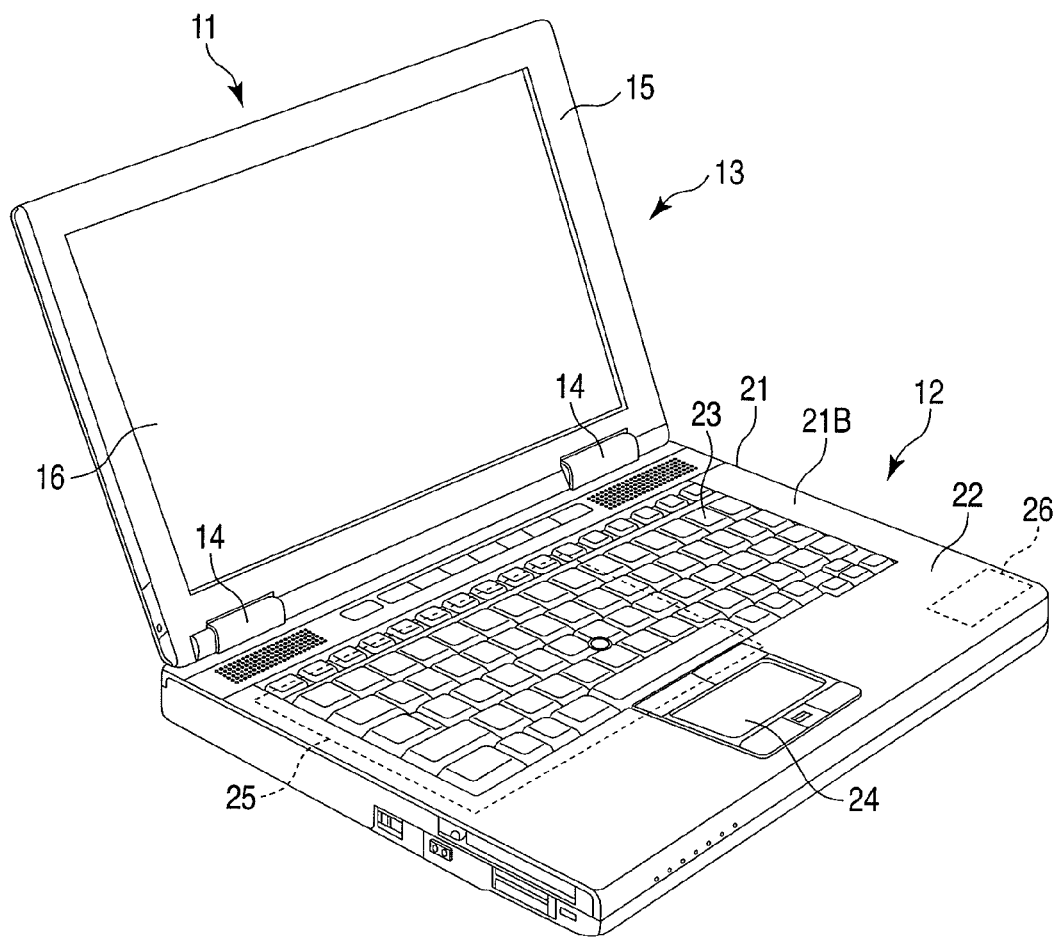
FIG. 1 is an exemplary diagram showing a perspective view of a portable computer as an example of the electronic device according to the first embodiment.

As shown in FIG. 1, a portable computer 11 includes a main body unit 12, a display unit 13, and a hinge portion 14 provided between the main body unit 12 and the display unit 13. The hinge portion supports the display unit 13 such as to be pivotable. With the hinge portion 14, the display unit 13 can pivote between a state where it is close to the main body 12 and another state where it is open with respect to the main body 12.

As shown in FIGS. 1 to 3, the display unit 13 includes a cover 15 and a liquid crystal display 16, which is an example of the display to be housed inside the cover 15. The cover 15 is formed into a shape of box, and made of, for example, of a synthetic resin.

Figure 5:
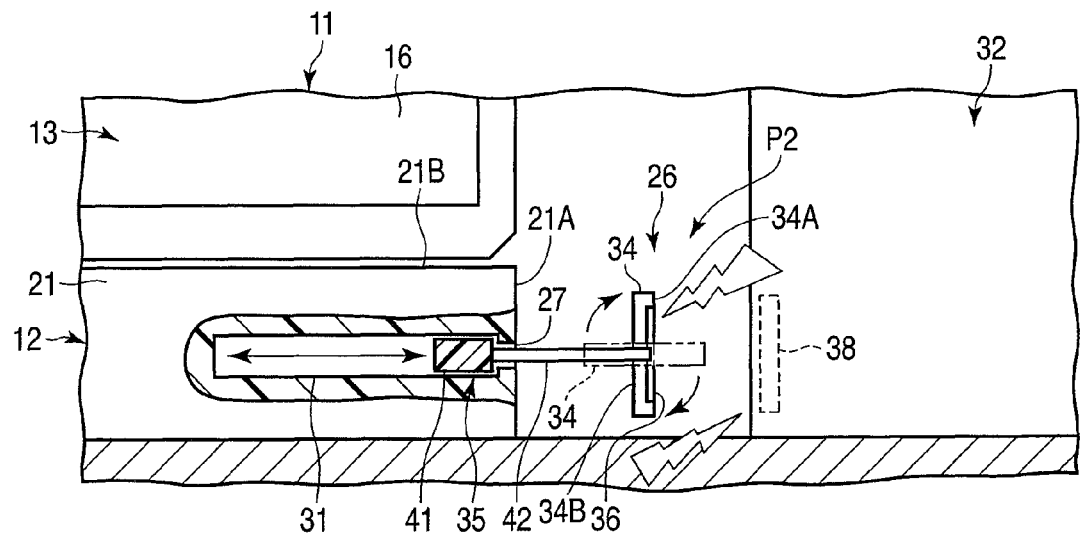
FIG. 5 is an exemplary front view of the portable computer shown in FIG. 1 in the first use mode in which it carries out short-distance radio communication with the first device.

The main body unit 12 includes a synthetic resin-made housing 21 having a box shape, a palm rest portion 22 provided in a front portion of the housing 21, a keyboard 23 and a touch pad 24 serving as a pointing device, which are mounted on the housing 21, and a printed circuit board 25 and an antenna unit 26, housed inside the housing 21. As shown in FIG. 5, the housing 21 has a slit-like opening portion 27 through which the antenna unit 26 is taken in or out of the housing 21, and a pair of groove portions 31 formed to continue to the opening portion 27. The slide portion 41 of the antenna unit 26, which will be described later, is slidable with respect to the pair of the groove portions 31.

The case where the first device 32 is placed on the right-hand side of the portable computer 11 to carry out short-distance radio communications will now be described as an example. As shown in FIGS. 1 and 5, the housing 21 includes a first face 21A which opposes the first device 32 of the other end in the short-distance radio communications and a second face 21B which normally crosses with the first face 21A. The opening portion 27 is made in the first face 21A. The antenna unit 26 is provided in the vicinity of the first face 21A. The second face 21B is a top face of the housing 21, and the palm rest portion 22 is formed in a part of the second face 21B. In this embodiment, the palm rest portion 22 also serves as a table portion on which the second device 33 of the other end in the short-distance radio communications is placed as will be explained later.

The antenna unit 26 includes an antenna 34 for short-distance radio communications and a support mechanism 35 which supports the antenna 34 to be pivotable. The antenna 34 is a loop antenna having a flat disk shape, and it is formed by printing a loop-shaped conductor pattern 36 on a printed wiring board. The antenna 34 includes a first face 34A which is a communication face on which the conductor pattern 36 is formed, and a second face 34B located on an opposite side. The short-distance radio communications carried out by the communication face are one of transmission, reception and transmission/reception of radio waves. The antenna 34 is in conformity with a communication standard of, for example, Transfer Jet (registered trademark).

The electromagnetic waves transmitted from this antenna 34 have directivity. The electromagnetic waves normally crosses with the first face 34A of the antenna 34 and is radiated in a direction opposite to the direction where the second face 34B is located. The antenna unit 26 is provided at a position underneath the palm rest portion 22 and also above a third built-in antenna 61 of a third device 37, which will be described later.

The support mechanism 35 is provided to be interposed between the housing 21 and the antenna 34. As shown in FIGS. 1 and 2, the support mechanism 35 includes a thick-plate slide portion 41 which is slidable with respect to the groove portions 31 of the housing 21, a pair of arm portions 42 extending in a parallel direction from the slide portion 41, and a shaft portion 43 set at distal end portions of the arm portions 42 and supported by the arm portions 42 such as to be pivotable. The shaft portion 43 extends from the distal ends of the arm portions 42 such as to be in parallel with the second face 21B of the housing 21. The shaft portion 43 is formed as an integral unit as the flat-disk antenna 34.

Figure 4:
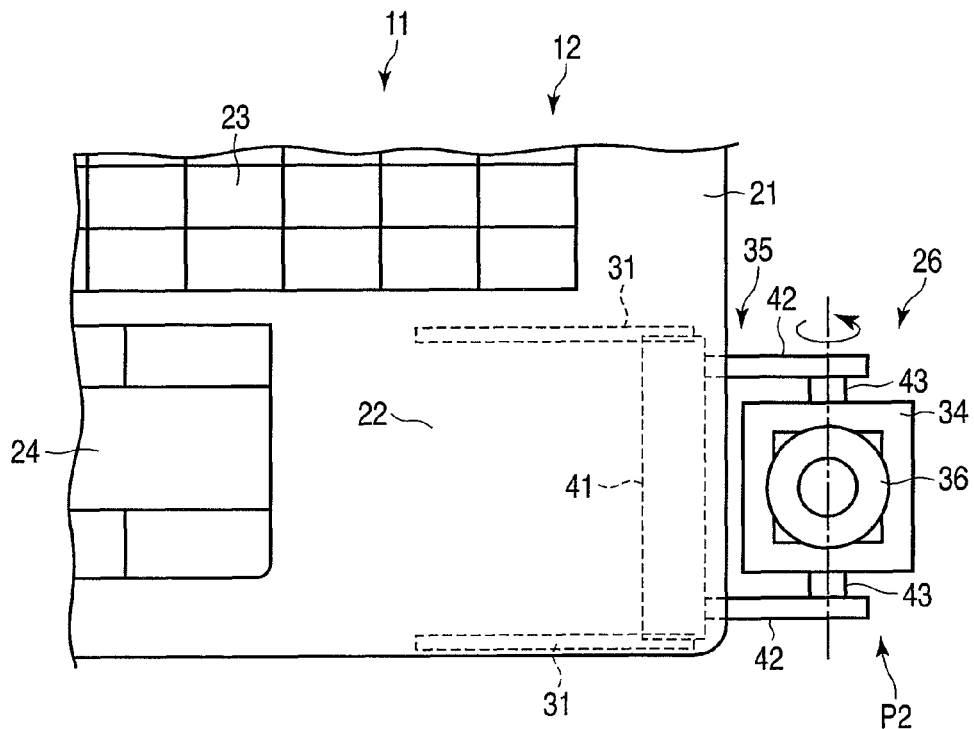
FIG. 4 is an exemplary top view of the antenna unit shown in FIG. 3 while it is in the second portion.

The support mechanism 35 can support the antenna 34 in such a manner that the antenna 34 moves by sliding between the first portion P1 where the antenna 34 is contained inside the housing 21 as shown in FIG. 3 and the second portion P2 where the antenna 34 is drawn to the outside from the housing 21 as shown in FIG. 4. As shown in FIG. 2, the antenna 34 integrated with the shaft portion 43 is pivotable with respect to the arm portions 42. As shown in FIG. 4, the antenna 34 is supported by the support mechanism 35 so as to be pivotable at the second portion P2.

Next, with reference to FIG. 5, the first use mode of the short-distance radio communications of the portable computer 11 according to this embodiment will now be explained. As shown in FIG. 5, the first device 32 serving as a party on the other side in the short-distance radio communications between the portable computer 11 and itself, is placed at a position side by side to the portable computer 11. As an example of the first device 32, a digital video camera is shown in FIG. 5. The first device 32 includes the first built-in antenna 38 embedded therein. The following explanation will be made for the case where the first face 34A of the antenna 34 faces upwards, taken as an initial position.

In order to carry out short-distance radio communications between the first device 32 and itself, first, the first device 32 is placed at such a position that the first built-in the antenna 38 is located in the vicinity of the antenna 34 of the portable computer 11. Then, the user manually moves the antenna unit 26 of the portable computer 11 from the first portion P1 to the second position P2, so as to expose the antenna 34 to the outside. Further, the user uses his or her finger to pivot the antenna 34 by 90 degrees from its initial position so that the antenna 34 normally crosses with the arm portions 42. In this manner, the first face 34A of the antenna 34 now faces the first built-in antenna 38 of the first device 32. Here, the distance between the first face 34A of the antenna 34 and the first built-in antenna 38 is, for example, several centimeters.

In this state, short-distance radio communications are carried out between the portable computer 11 and the first device 32 and thus video data, music data, etc. are transmitted and received. After the completion of the short-distance radio communication, the antenna 34 is pivoted again back to the initial position, and then the antenna 34 now located in the second position P2 is moved to the first position P1 to be contained inside the housing 21.

Figure 6:
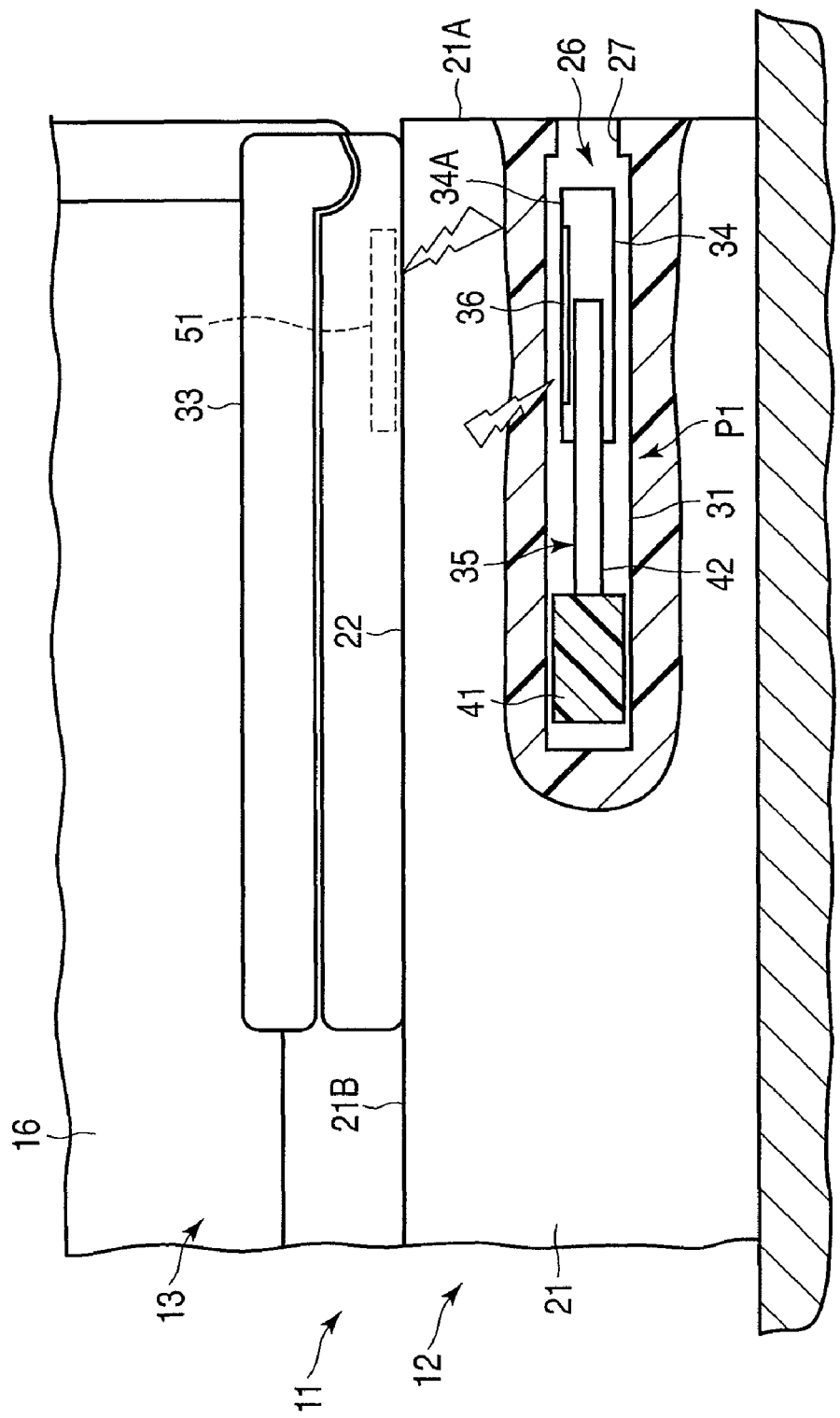
FIG. 6 is an exemplary front view of the portable computer shown in FIG. 1 in the second use mode in which it carries out short-distance radio communication with the second device.

Next, with reference to FIG. 6, the second use mode of the short-distance radio communications of the portable computer 11 will now be explained. In this use mode, a mobile telephone is shown as an example of the second device 33 serving as a party on the other side in the short-distance radio communications. The second device 33 is placed on an upper side of the palm rest portion 22 of the main body unit 12. In this use mode, the user first places the second device 33 on an upper side of the palm rest portion 22 such that the second built-in antenna 51 embedded in the second device 33 is located in the vicinity of the antenna unit 26 of the portable computer 11. Here, although it is not used in this embodiment, a mark may be formed on the upper side of the palm rest portion 22 so that the user can more easily locate the portion where the second device 33 should be placed intuitively.

Then, the user draws the antenna unit 26 out from the first position P1 to the second portion P2 and confirms whether or not the first face 34A, which is the communication face of the antenna 34 is located correctly at the initial position, that is, whether or not the antenna 34 is positioned such that the first face 34A faces upwards. After that, while the first face 34A being at the initial position, the antenna unit 26 is moved back from the second position P2 to the first position P1. Thus, the first face 34A of the antenna 34 now faces the second built-in antenna 51 of the second device 33. In this manner, an appropriate communication distance (several centimeters) is assured between the portable computer 11 and the second device 33, thereby making it possible to carry out a smooth short-distance radio communication.

In the case where it becomes hard to operate on the keyboard 23 of the portable computer 11 by placing the second device 33 on the palm rest portion 22, the second device 33 is placed at a position side by side to the portable computer 11, and the antenna 34 is drawn out to the second position P2, where it is pivoted by 90 degrees towards the second device 33. Thus, the user can shift easily from the second use mode to the first use mode.

Figure 7:
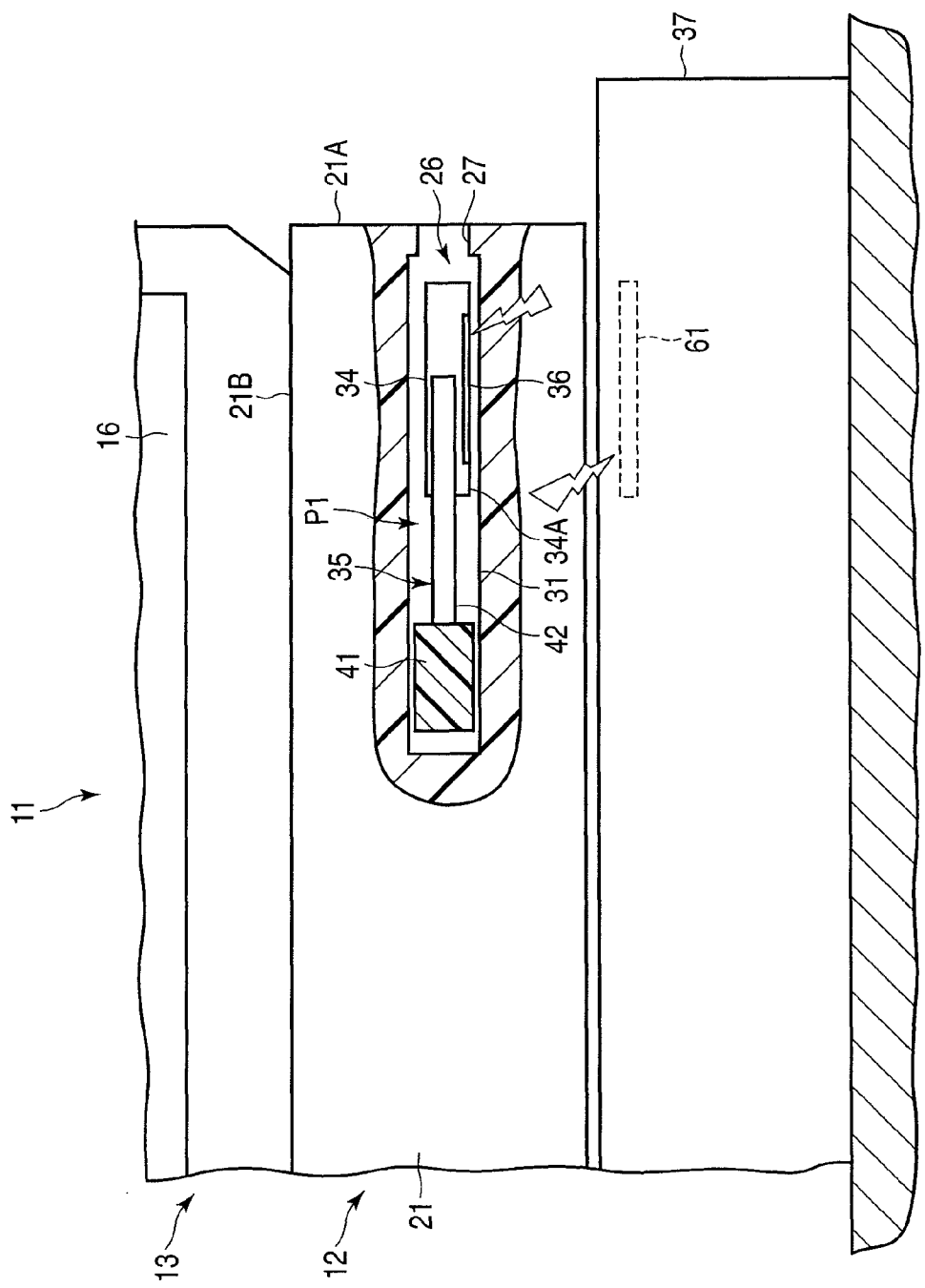
FIG. 7 is an exemplary front view of the portable computer shown in FIG. 1 in the third use mode in which it carries out short-distance radio communication with the third device.

Next, with reference to FIG. 7, the third use mode of the short-distance radio communications of the portable computer 11 will now be explained. In this use mode, a docking station is shown as an example of the third device 37 serving as a party on the other side in the short-distance radio communications. The docking station is used to connect the portable computer 11 to an external peripheral device such as an external keyboard, printer or external monitor.

In the third use mode, first, the main body unit 12 of the portable computer 11 is placed at a predetermined position on the upper surface of the third device 37. The docking station, which is the third device 37, is a device exclusively for the portable computer 11. Therefore, the third built-in antenna 61 embedded therein is set such as to be placed in the vicinity of the antenna unit 26 of the portable computer 11. In other words, the antenna 34 of the portable computer 11 is arranged to be placed above the third built-in antenna 61 of the third device 37.

In the third use mode, only by placing the portable computer 11 on the third device 37, the positioning of the antenna 34 and the third built-in antenna 61 with respect to each other is completed. Then, the user draws out the antenna unit 26 from the first portion P1 to the second position P2, and pivots the antenna 34 by 180 degrees from its initial position so that the first face 34A, which is the communication face of the antenna 34, faces downwards. Then, the antenna unit 26 now at the second position P2 is set back to be contained in the first position P1. In this state, the antenna 34 and the third built-in antenna 61 face each other to assure an appropriate communication distance therebetween, thereby making it possible to carry out the short-distance radio communication.

Figure 8:
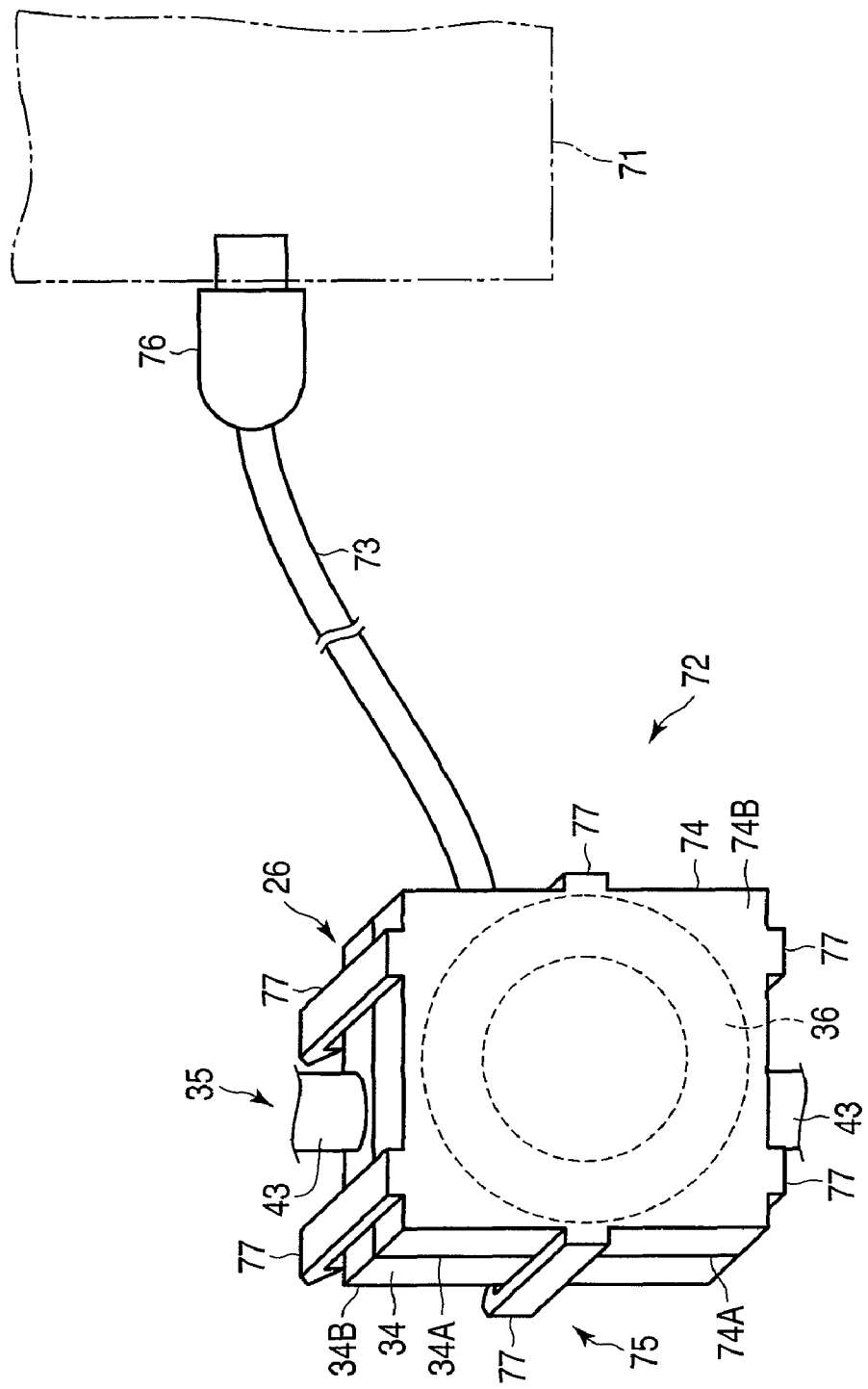
FIG. 8 is an exemplary perspective view of the portable computer shown in FIG. 1 in the fourth use mode in which it carries out short-distance radio communication with the fourth device.

Next, with reference to FIG. 8, the fourth use mode of the short-distance radio communications of the portable computer 11 will now be explained. In this use mode, a digital video camera is shown as an example of the fourth device 71 serving as a party on the other side in the short-distance radio communications. In this use mode, a cable-equipped antenna 72 of the portable computer 11 is used.

The cable-equipped antenna 72 includes a cable 73 to be connected to the fourth device 71, a second antenna 74 provided at a distal end of the cable 73 and opposing the antenna 34, and a lock mechanism 75 which secure the second antenna 74 to the antenna 34 of the portable computer 11. The cable 73 includes, for example, a USB connector 76 which conforms to USB (universal serial bus) at an end portion opposite to the end portion where the second antenna 74 is provided. Further, the cable-equipped antenna 72 includes a conversion circuit for converting signals between Transfer Jet (registered trademark) and USB.

The second antenna 74 has substantially the same structure as that of the antenna 34 of the portable computer 11. The second antenna 74 is in conformity with a communication standard of, for example, Transfer Jet (registered trademark). The second antenna 74 is a loop antenna having a flat disk shape, and it includes a first face 74A which is a communication face on which a loop-shaped conductor pattern 36 is printed on a printed wiring board, and a second face 74B located on an opposite side thereto.

The lock mechanism 75 includes, for example, 6 nail portions 77 which project from the second antenna 74 to engage with the antenna 34. The lock mechanism 75 can hold the antenna 34 in such a manner that the second antenna 74 correctly faces against the antenna 34. The six nail portions 77 are arranged respectively at positions offset from the shaft portion 43 of the antenna unit 26. With this arrangement, the nail portions 77 and the shaft portion 43 do not interfere with each other when the second antenna 74 is secured onto the antenna 34.

In the fourth use mode, first, the USB connector 76 of the cable-equipped antenna 72 is connected to the connector of the fourth device 71. Then, the first face 74A of the second antenna 74 is justly joined to the first face 34A of the antenna 34, and the second antenna 74 is secured to the antenna 34 by using the lock mechanism 75. In this state, the antenna 34 and the second antenna 74 are substantially in contact with each other, and therefore short-distance communication is smoothly carried out therebetween.

The above-provided description is an embodiment of the portable computer 11. According to this embodiment, the portable computer 11 includes the housing 21, the antenna 34 for short-distance radio communication, provided with a communication face through which short-distance radio communication is carried out, and a support mechanism 35 interposed between the housing 21 and the antenna 34, rendering the antenna 34 to be slidable between the first position P1 where the antenna is contained inside the housing 21 and the second position P2 where the antenna is drawn out of the housing 21, and supporting the antenna 34 to be pivotable at the second position P2.

With this structure, the antenna 34 is pivoted at the second position P2 where it is drawn out from the housing 21. Therefore, the user can directly adjust the set angle of the antenna 34 while visually checking it. In this manner, the antenna 34 can be correctly set to oppose the device on the other side of the short-distance radio communication, and thus the reliability of communication in the short-distance radio communication can be improved. Further, with the above-described structure, the user is able to visually check if the antenna 34 is correctly set, and thus the user's concerning about the position of the antenna can be removed. Further, the communication error caused by the inappropriate set angle of the antenna 34 can be prevented. When the antenna 34 is structured to be slidable and pivotable as described above, it can flexibly handle various types of communication styles which are diversifying. Further, with the structure in which the antenna 34 is pivoted at the second position P2, the thickness required to install the antenna 34 can be reduced as compared to the structure in which it is pivoted at the first position P1 which is inside the housing 21, and therefore the housing 21 can be thinned. In this manner, the present invention is able to meet the demands of the market of recent years, thinning and downsizing.

This housing includes the first face 21A and the first face 21A opposes the first device 32 of the other end in the short-distance radio communications, which is arranged side by side. The antenna 34 is provided in the vicinity of the first face 21A. With this structure, the antenna 34 can be located at a position close to the first device 32, and therefore the short-distance radio communication with respect to the first device 32 can be smoothly carried out.

The housing 21 includes the second face 21B which normally crosses with the first face 21A, and the support mechanism 35 includes the arm portions 42 extending in parallel with the second face 21B. The antenna 34 is supported to be pivotable via the shaft portion 43 set on the distal end portions of the arm portions 42. With this structure, the antenna 34 can be formed pivotable with a simple structure which utilizes one shaft portion 43. Further, since the shaft portion 43 extends in a direction parallel to the second face 21B, the space required to install the shaft portion 43 can be made as small as possible. With this structure, the housing 21 can be made thin as possible even if a pivot mechanism is provided.

The antenna 34 has a flat disk shape. With this shape, the thickness required to install the antenna 34 can be reduced, and thus the housing 21 can be formed to be further thin. The housing 21 includes the palm rest portion 22 which also serves as a table portion on which the second device 33 of the other end in the short-distance radio communications is placed, and the antenna 34 is located at a position underneath the palm rest portion 22.

With the above-described structure, the palm rest portion 22 can also serves as a table portion for the second device 33, and therefore the overall structure can be simplified as compared to the case where a separate table portion is provided on the portable computer 11. It should be noted usually a ground layer formed by application of a conductive metal is provided on the inner surface of the housing 21, thereby preventing electromagnetic waves from leaking from the inside of the housing 21 to the external environment. However, it is desirable that a ground-layer-free region should be provided at a position underneath the palm rest portion 22, so as to enable a smooth short-distance radio communication.

The housing 21 is placed on an upper side of the built-in antenna-containing third device 37 which serves as a party on the other side of the short-distance radio communication. The antenna 34 is located at a position above the third built-in antenna 61. With this structure, the first face 34A of the antenna 34 is pivoted to face downwards by the support mechanism 35, and it is, while maintaining this state, arranged at the first position P1. In this manner, the first face 34A of the antenna 34 and the built-in antenna of the third device 37 can be set to face each other. Thus, a smooth short-distance radio communication can be carried out with the third device 37 as well, situated underneath the housing 21. It is also preferable as in the above-described case that the ground layer should not be provided at a position between the antenna 34 and the third built-in antenna 61.

Further, the portable computer 11 comprises the cable-equipped antenna 72, which includes the cable 73 to be connected to the fourth device 71 which serves as a party on the other side of the short-distance radio communication, and the second antenna 74 provided at the distal end of the cable 73 to face the antenna 34, which carries out short-distance radio communications with respect to the antenna 34.

With this structure, a smooth radio communication can be carried out with respect to the fourth device 71 as well, which does not include an antenna which conforms to short-distance radio communications. To be provided with a cable-equipped antenna is particularly useful in the respect that it becomes able to have compatibility with conventional types of interface until a new communication mode is widespread.

The cable-equipped antenna 72 includes the lock mechanism 75 which holds the second antenna 74 such as to correctly face against the antenna 34. In some sections of the second antenna 74, the cable 73 is vended, and the second antenna 74 and the cable 73 may be moved in some cases due to the elasticity of the cable 73. With the structure of this embodiment, even if the second antenna 74 receives such a force, the second antenna 74 does not move, and thus the second antenna 74 can be set to face the antenna 34.

Apart from the above, the electronic device of the present invention is not limited to the modes of the above-mentioned embodiments. In the embodiment, the antenna unit 26 is contained inside the housing 21 of the main body unit 12; however it is alternatively possible that the antenna unit 26 is contained inside the cover 15 of the display unit 13. Further, the electronic device of the present invention can be applied to mobile telephones and the like. Moreover, it is only natural that the electronic device of the present invention can be remodeled into various versions when actually carrying it out as long as the essence of the invention does not fall out of the scope thereof.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An electronic device comprising:
a housing having a palm rest portion;
a flat antenna for short-distance radio communication, comprising a communication face configured to execute a short-distance radio communication on one of surfaces of the flat antenna; and
a support mechanism between the housing and the antenna configured to support the antenna to be slidable between a first position where the antenna is inside the housing and a second position where the antenna is outside of the housing, and also to be pivotable at the second position,
wherein the antenna is locatable at the first position under a first condition where the communication face faces to a direction of the palm rest portion and a second condition where the communication face faces to an opposite direction to the direction of the palm rest portion.

2. The electronic device of claim 1, wherein:
the housing comprises a second face including the palm rest portion and a first face crossing with the second face; and
the antenna is in a vicinity of the first face.

3. The electronic device of claim 2, wherein:
the support mechanism comprises a shaft extending in parallel with the second face, the antenna being supported pivotably by the shaft.

4. The electronic device of claim 3, wherein:
the housing comprises the palm rest portion which also is a table portion for a second device which is a counterpart of the short-distance radio communication; and
the antenna is underneath the palm rest portion.

5. The electronic device of claim 4, wherein:
the antenna is on an upper side of a third device which is a counterpart of the short-distance radio communication, and the housing is on the third device.

6. The electronic device of claim 5, further comprising: a cable-equipped antenna comprising a cable configured to connect to a fourth device which is a counterpart of the short-distance radio communication, and a second antenna at a first end of the cable facing the antenna, configured to execute short-distance radio communications with respect to the antenna.

7. The electronic device of claim 6, wherein:
the cable-equipped antenna comprises a lock configured to hold the second antenna such that the second antenna is configured to face against the antenna.

8. An electronic device comprising:
a housing;
a flat antenna for short-distance radio communications, comprising a communication face configured to execute a short-distance radio communication on one of surfaces of the flat antenna; and
a support mechanism between the housing and the antenna configured to support the antenna to be slidable between a first position where the antenna is inside the housing and a second position where the antenna is outside of the housing, and also to be pivotable at the second position,
wherein the support mechanism comprises a pair of arm portions extending to the sliding direction and a shaft portion provided at a distal end of the arm portions and supported pivotably by the arm portions, and the antenna is supported pivotably by the shaft portion.

9. An electronic device comprising:

a housing;

a flat antenna for short-distance radio communications, comprising a communication face configured to execute a short-distance radio communication on one of surfaces of the flat antenna; and a support mechanism between the housing and the antenna configured to support the antenna to be slidable between a first position where the antenna is inside the housing and a second position where the antenna is outside of the housing, and also to be pivotable at the second position.

* * * * *